United States Patent [19]
Cavalletti et al.

[11] Patent Number: 5,618,823
[45] Date of Patent: Apr. 8, 1997

[54] GLUTATHIONE AS CHEMOPROTECTIVE AGENT

[75] Inventors: Ennio Cavalletti; Sergio Tognella, both of Milan, Italy

[73] Assignee: Boehringer Mannheim Italia S.p.A., Milan, Italy

[21] Appl. No.: 351,403

[22] PCT Filed: Jun. 14, 1992

[86] PCT No.: PCT/EP93/01494

§ 371 Date: Dec. 22, 1994

§ 102(e) Date: Dec. 22, 1994

[87] PCT Pub. No.: WO94/00141

PCT Pub. Date: Jan. 6, 1994

[30] Foreign Application Priority Data

Jun. 24, 1992 [IT] Italy .................. MI92A1551

[51] Int. Cl.⁶ .............. A61K 31/44; A61K 31/335; A61K 31/195
[52] U.S. Cl. .............. 514/283; 514/449; 514/562
[58] Field of Search .............. 424/10; 514/283, 514/449, 562

[56] References Cited

FOREIGN PATENT DOCUMENTS 0265719 5/1988 European Pat. Off. .................. 424/10

OTHER PUBLICATIONS

Seminars in Oncology, vol. 18, No. 1, Feb. 1991, pp. 1–4.
Neroreport, vol. 2, No. 6, Jun. 1991, pp. 345–347.
The Merck Index, 11th Ed, 1989, Merck & Co., Inc., Rahway, N.J., U.S.A.
WO,A,8 602 353, Apr. 24, 1986.
WO,A,9, 102 810, Mar. 7, 1991.

*Primary Examiner*—Jerome D. Goldberg
*Attorney, Agent, or Firm*—Nikaido, Marmelstein, Murray & Oram LLP

[57] ABSTRACT

The use of glutathione (GSH) as chemoprotective agent against neurotoxicity induced by antitumor drugs active on the mitotic fuse is herein described.

2 Claims, No Drawings

GLUTATHIONE AS CHEMOPROTECTIVE AGENT

This application is a 371 PCT/EP 93/01494 filed Jun. 14, 1992.

The present invention relates to the use of reduced glutathione (GSH) as protecting agent towards neurotoxicity induced by antitumor drugs active on the mitotic fuse.

Examples of such drugs include Vinca alkaloids, such as vincristine and vinblastine, and cyclotaxan derivatives, whose parent compound, i.e. taxol, is presently under advanced clinical trial (Anti-Cancer Drugs, 2, 1991, page. 519–530).

The most serious limitation to the success of antineoplastic chemotherapy resides in the severe toxicity annexed to the use of antitumor drugs: toxic symptoms limit administrable doses, they affect treatment cycles and seriously jeopardize the life quality of the oncologic patient.

The high toxicity of the antitumor drugs is due to the lack of selective activity of the drugs themselves, which, besides hitting the tumor cells, interact with other organs or cell populations in the human body.

Toxic symptoms deriving from the treatment with antitumor compounds are therefore strictly connected with the chemical structure of the compounds and with their mechanism of action. For example, anthracycline induced cardiotoxicity was strictly related to the quinone substructure typical of anthracyclines. In fact, this structure undergoes in vivo a single-electron reduction, thus forming the emiquinone radical. This last compound is capable of promoting the avalanche formation of free oxygen radicals, which, in their turn, are responsible for the cardiac tissue damage. Not by chance several radical scavengers are able to perform a protective effect lowering the anthracycline cardiotoxicity.

As another example, cis-platin is an antitumor agent which is endowed with heavy organo-specific toxicities, particularly relevant especially towards kidney. In fact, cis-platin, when absorbed by kidney, forms the diaquo species by loss of two chlorine ions This happens since in the renal tubule the concentration of chlorine ions is lower than in blood. So activated cis-platin is capable of damaging the tubules with resulting nephropathy. Several thiol compounds, among which diethyldithiocarbamate and glutathione are able to protect kidney from the cis-platin effect, since they accumulate at kidney level and probably interact with the compound.

Cis-platin is known to cause neurotoxic effects too (Eur. J. Cancer Vol. 27(3), 1991, 372–376), which several protective agents have been evaluated towards. among these, nimodipine (Eur. J. Pharmacol. 1990, 183, 1710–1711) and ACTH (4–9) neuropeptide (Eur. J. Cancer Clin. Oncol. 1988, 89, 81–87) turned out to be the most. effective.

Also glutathione and other sulphur compounds (thiosulfate, ethiofos, diethyldithiocarbamate) resulted effective to different extents in the prevention of cis-platin neurotoxicity (Tumori, 1987, 73, 337–340, EP-A-0265719 Cancer Res., 1993, 53, 544–549), presumably as an effect coming from the nephrotoxicity protection, which is widely described especially for glutathione. An uncompromised kidney functional capacity would assure an effective and ready elimination of cis-platin, thus avoiding the accumulation and the resulting toxicity towards other tissues or target cells.

From the whole of the data reported in clinical and pharmacological literature, it comes out that a single agent capable of protecting indiscriminately from the toxic effects of any antitumor compound does not exist. It is neither foreseen that a compound capable of limiting or nullifying the toxicity of a certain antitumor drug can also exert a protecting effect from the toxicity of another antitumor drug belonging to a different chemical class and having a different activity mechanism.

On the other hand, vinca alkaloids and cyclotaxans derivatives, such as taxotere and taxol, characterized by the same cytotoxic mechanisms at microtubule level, share, as unwished side effect, neurotoxicity against peripheral nerve (Neurology, 39, 1980, 368–37; Neuroscience 10(2), 1983, 491–509; J. Neurocytol. 15, 1986, 483 J. Clin. Oncol. 9, 1991, 1261–7). To date, only one study exists about the possibility to fight against vinca alkaloids neurotoxicity by using gangliosides as exogen chemoprotective agents (Cancer Chemother. Pharmacol. 26, 31–36, 1990).

It has now been found that the neuropathy, induced by vinca alkaloids and cyclotaxans derivatives, can significantly be reduced if not totally prevented by means of a pretreatment with reduced glutathione.

This finding comes out to be absolutely surprising even in the light of the fact that reduced glutathione previously proved to be unable to effectively contrast the neurotoxicity characteristics of other classes of drugs, particularly ototoxicity of the aminoglycoside antibiotics.

According to the invention, reduced glutathione can be administered from about 2 hours to about 15 minutes before administering the antimitotic drug. Reduced glutathione can be administered whether orally or parenterally, in doses ranging from 5 to 500 mg/kg, preferably from 30 to 100 mg/kg. Generally, it has been found that administering from 1 to 5 g of glutathione, preferably 30 minutes before the administration of the antimitotic drug, is capable of giving the most promising results.

Protecting activity is verifiable also when more antitumor drugs are administered at the same time, as in polychemotherapy protocols. In the case where vinca alkaloids and/or taxol or its derivatives are combined, for example, with platinum complexes, such as cis-platin, carboplatin and the like, the previously administered reduced glutathione will exert a global protective effect both on the typical nephrotoxicity of platinum complexes and on the neurotoxicity of alkaloids and taxol or derivatives. Evident therapeutical advantages come out from the present invention, which are particularly significant in the case of bladder, ovary and testicle carcinomas, wherein said combinations are in fact already used or are under evaluation.

Vinca alkaloid and taxol dosages are the only already described for this kind of drugs, but it can optionally be raised, thanks to the GSH chemoprotective effect, with consequent improvement of the response to the treatment.

A preferred embodiment of the invention relates to pharmaceutical compositions consisting of separated administration forms for sequential or separated use containing 1) reduced glutathione and 2) an antitumor drug active on the mitotic fuse. Taxol is particularly preferred as antitumor drug.

Typical administration forms comprise lyophilized ampoules to be reconstituted with a suitable sterile solvent (for example saline or glucosated solution), ready-for-use sterile solutions and, optionally, also capsules, tablets, syrups and other forms suitable to oral administration. In the case of the more common infusion administration, for example, a pharmaceutical formulation containing 1 to 5 g of GSH, preferably 2.5 g, is diluted to a total volume of 50 to 500 ml with saline and infused within 15 minutes before the administration.

The present invention is further illustrated, by way of example, by the results from pharmacotoxicological tests using taxol and GSH.

EXAMPLE

Materials and Methods

Animals and Animal Care

The test was carried out in adult male Wistar rats, weighing from 200 to 220 g. The animals were housed in macrolon cages with free access to feed and water and sawdust as bedding. Each cage housed 4 rats. Dark-light cycle was 12 hours, with light from 7.30 a.m. to 7.30 p.m.

Drugs

A stock solution was prepared by dissolving taxol in a suitable solvent. This solution was further diluted with saline immediately before use. GSH was dissolved in distilled water at the concentration of 125 mg/ml.

Experimental Design

Three groups of 8 animals each were subjected to treatment with vehicle+distilled water (age-matched controls), taxol+distilled water, taxol+GSH, respectively. Bodyweight was measured daily and taxol was dosed accordingly. The animals were injected with taxol 1.2 mg/kg/day (final concentration 0.3 mg/ml) 5 days a week for 7 weeks; during the next 2 weeks a dose of 2.4 mg/kg/day (final concentration 0.6 mg/ml) 5 days a week was administered (cumulative dose: 66 mg/kg). GSH was intravenously administered at the dose of 500 mg/kg 30 min before each taxol injection.

Electrophysiology

Electrophysiological determinations were carried out on animals under general anaesthesia with Hypnorm containing 10 mg/ml fluanisone and 20 mg/ml fentanyl citrate at the dose of 0.8 ml/kg. Sensitive nerve conduction velocity with respect to H reflex (HSNCV) was measured according to the method described by De Koning et al., Neurotoxic side-effects of cisplatin; Eur. J. Cancer, 27: 372–6, (1991). H. Reflex is a long latency reflex which occurs in response to the stimulation of the sensitive afferent fiber which monosynapticaily excites $\alpha$-motoneurons of the spinal cord. HSNCV was calculated dividing the distance between two points of stimulation by the difference between H latencies which were recorded at both sites.

Data Analysis

Statistical evaluation of the experimental data was performed by an analysis of variance for repeated measurements (ANOVAR) followed by supplemental t tests. The treatment code was opened only after this analysis was completed.

Results

General Toxicity

During the first 7 weeks (taxol dose 6 mg/kg/week) the taxol treated animals continued to grow almost as fast as the age-matched control. After doubling the dose, however, the animals lost weight and taxol administration had to be discontinued two weeks later, especially as two (out of eight) animals co-treated with saline died during the electrophysiological measurement at the end of this treatment period. During the next 4 weeks no further taxol was administered but two other animals in the taxol/saline group died, one during anesthesia at week 10 and another during the measurement at week 13.

Electrophysiolgy

In the age-matched controls, HSNCV reached normal adult values toward the end of the experiment. A sensory neuropathy, as evidenced by a significant decrease of the HSNCV, developed in the taxol/distilled water treated animals from week 5 onwards. The HSNCV of taxol/GSH treated animals did not significantly differ from that of the age-matched controls.

The protective effect of GSH against taxol neurotoxicity has also been confirmed by behavioural studies ("retail flick test"), SNCV measurements in the caudal nerve, and morphological and morphometric examination of primary sensitive ganglia and ischiatic and saphenous nerves in rats subjected to: i) "subacute" administration of either 5 or 10 mg/kg/day i.p. of taxol diluted in DMSO for 5 consecutive days; ii) "chronic" administration of either 10 or 20 mg/kg/day i.p. of taxol diluted in DMSO once a week for 5 weeks.

We claim:

1. A method of treating a patient, comprising administering to said patient reduced glutathione, subsequently administering to said patient an antitumor effective amount of a drug which is active on the mitotic fuse, said antitumor drug being selected from vinblastine and taxol, the amount of said reduced glutathione being effective to protect said patient against neurotoxicity against peripheral nerve caused by said drug.

2. The method in claim 1, wherein taxol is the antitumor drug.

* * * * *